United States Patent [19]
Okada

[11] Patent Number: 6,002,791
[45] Date of Patent: Dec. 14, 1999

[54] PHOTOMASK INSPECTION APPARATUS

[75] Inventor: Takehiko Okada, Tokyo, Japan

[73] Assignee: NEC Corporation, Tokyo, Japan

[21] Appl. No.: 08/907,736

[22] Filed: Aug. 8, 1997

[30] Foreign Application Priority Data

Aug. 9, 1996 [JP] Japan ................................ 8-211070

[51] Int. Cl.⁶ .................................................. G06K 9/00
[52] U.S. Cl. ........................... 382/144; 382/145; 348/125
[58] Field of Search ............................. 356/394; 382/144, 382/141, 145, 147, 149, 150; 348/86, 125, 126, 129, 131, 132

[56] References Cited

U.S. PATENT DOCUMENTS 5,767,974  6/1998  Higashiguchi et al. ............... 356/394

FOREIGN PATENT DOCUMENTS

| 58-27323 | 2/1983 | Japan . |
| 61-216428 | 9/1986 | Japan . |
| 2-108947 | 4/1990 | Japan . |
| 2-116740 | 5/1990 | Japan . |
| 3-51747 | 3/1991 | Japan . |

Primary Examiner—Joseph Mancuso
Assistant Examiner—Vikkram Bali
Attorney, Agent, or Firm—Foley, Hoag & Eliot LLP

[57] ABSTRACT

A photomask inspection apparatus includes a photoelectric converting portion, a first comparator, buffer memories, a design data converting portion, and second and third comparators. The photoelectric converting portion converts the respective beams of light having separately scanned adjoining identical unit patterns formed on a photomask into electrical signals. The first comparator compares these electrical signals with each other to find whether there is any inconformity between the unit patterns, and when any inconformity is found, the first comparator outputs coordinate information of the inconformity. The buffer memories store the electrical signals respectively when the inconformity is found by the first comparator. The design data converting portion converts only design data of peripheral coordinates of the coordinate information in the design data stored in the external memory into an inspection signal. The second and third comparators compare the electrical signals from the buffer memories with the inspection signal to identify a photomask pattern having a defect.

6 Claims, 2 Drawing Sheets

PHOTOMASK INSPECTION APPARATUS

BACKGROUND OF THE INVENTION

The present invention relates to a photomask inspection apparatus and, more particularly, to a photomask inspection apparatus to be used upon manufacturing semiconductor integrated circuit.

There are two inspection methods for inspecting a defect on a photomask. A first inspection method is a pattern comparison method in which adjacent unit patterns are compared with each other to inspect the difference therebetween. A second inspection method is a database verifying inspection method in which an actual pattern is compared with a design pattern to make an inspection.

A photomask inspection apparatus capable of simultaneously executing the inspections according to the above-mentioned two methods is disclosed in Japanese Patent Laid-Open Publication No. Hei 2-108947. FIG. 2 is a structural view of the apparatus disclosed by the above reference. As shown in the figure, a central control unit 12 operates so that a flush switch 3 turns on light sources 4R and 4L, and then optical signals $D_{R1}$ and $D_{L1}$ from right and left unit patterns 2R and 2L on a mask 2, which has been obtained through lenses 5R and 5L, are converted into comparison signals $D_{R2}$ and $D_{L2}$ by a photoelectric converting portion 6.

The comparison signal $D_{R2}$ is subjected to intensity adjustment and division by an amplifier 13 and a division circuit 14 so as to be converted into signals $D_{R3}$ and $D_{R4}$ which are inputted into two comparators 9a and 9b respectively. The comparator 9a compares the comparison signal $D_{L2}$ with the signal $D_{R3}$ and stores defect information obtained by the pattern comparison method between the unit patterns 2L and 2R on the photomask 2 into a buffer memory 10a.

On the other hand, the comparator 9b compares the comparison signal $D_{R4}$ with a comparison signal $D_2$ which is generated by a design data converting portion 8 from design data $D_1$ recorded in an external memory 7, and stores defect information obtained by the database verifying inspection method into a buffer memory 10b. When an output instruction is inputted from a console 1, each defect information stored in the buffer memories 10a and 10b is outputted to an external output unit 11.

However, in the above conventional photomask inspection apparatus, since the defect information shown in the external output unit 11 must be analyzed, there are some cases where it is difficult to determine which of adjoining chips contains defects such as an error in size of a contact hole.

Further, in the conventional photomask inspection apparatus, since the design data converting portion 8 must convert all the design data in the external output unit 11, there is a problem that a long time is required to convert the design data.

SUMMARY OF THE INVENTION

An object of the present invention is to provide a photomask inspection apparatus capable of determining which of adjoining chips contains a defect.

Another object of the present invention is to provide a photomask inspection apparatus capable of shortening a data conversion time and executing inspection at high speed.

A photomask inspection apparatus according to the present invention comprises a measuring system for converting the respective beams of light, which have separately scanned two adjoining identical unit patterns formed on a photomask, into a first electrical signal and a second electrical signal, comparing the first and second electrical signals with each other to detect whether or not the adjoining identical unit patterns are inconformity with each other, and when inconformity is found, outputting coordinate information of the inconformity; first and second memory circuits for storing the first and second electrical signals when the inconformity is found by the measuring system; a third memory circuit for storing design data of a pattern formed on the photomask; and identifying means for identifying a photomask pattern having a defect by comparing an inspection signal obtained from the design data stored in the third memory circuit with output signals from the first memory circuit and the second memory circuit respectively.

With the above construction, when there is a difference between two adjoining identical unit patterns (adjoining chips) formed on the photomask, the output signals are compared with the design data so that it is possible to automatically determine which of the adjoining chips contains the defect.

Further, since there is provided a design data converting portion for converting only design data of peripheral coordinates including the coordinate information from the measuring system in design data stored in the third memory circuit, if there is a difference between the adjoining chips, only the design data of the periphery of the coordinate information in the stored design data is converted into the inspection signal.

BRIEF DESCRIPTION OF THE DRAWINGS

The above and other objects, advantages and features of the present invention will be more apparent from the following description taken in conjunction with the accompanying drawings, in which.

DETAILED DESCRIPTION OF THE INVENTION

Figure 1:
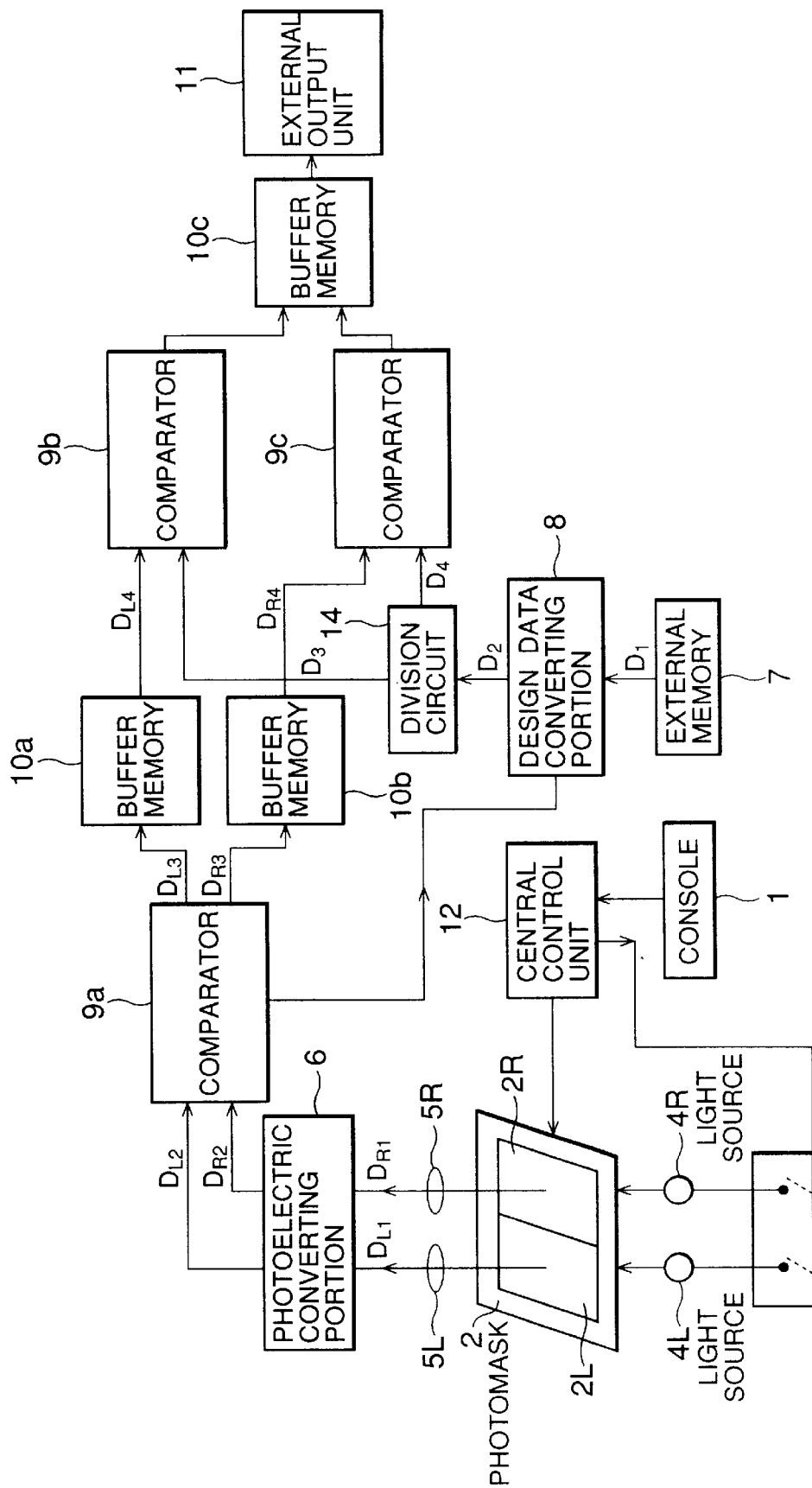
FIG. 1 is a structural view of an embodiment of the present invention.
Figure 2:
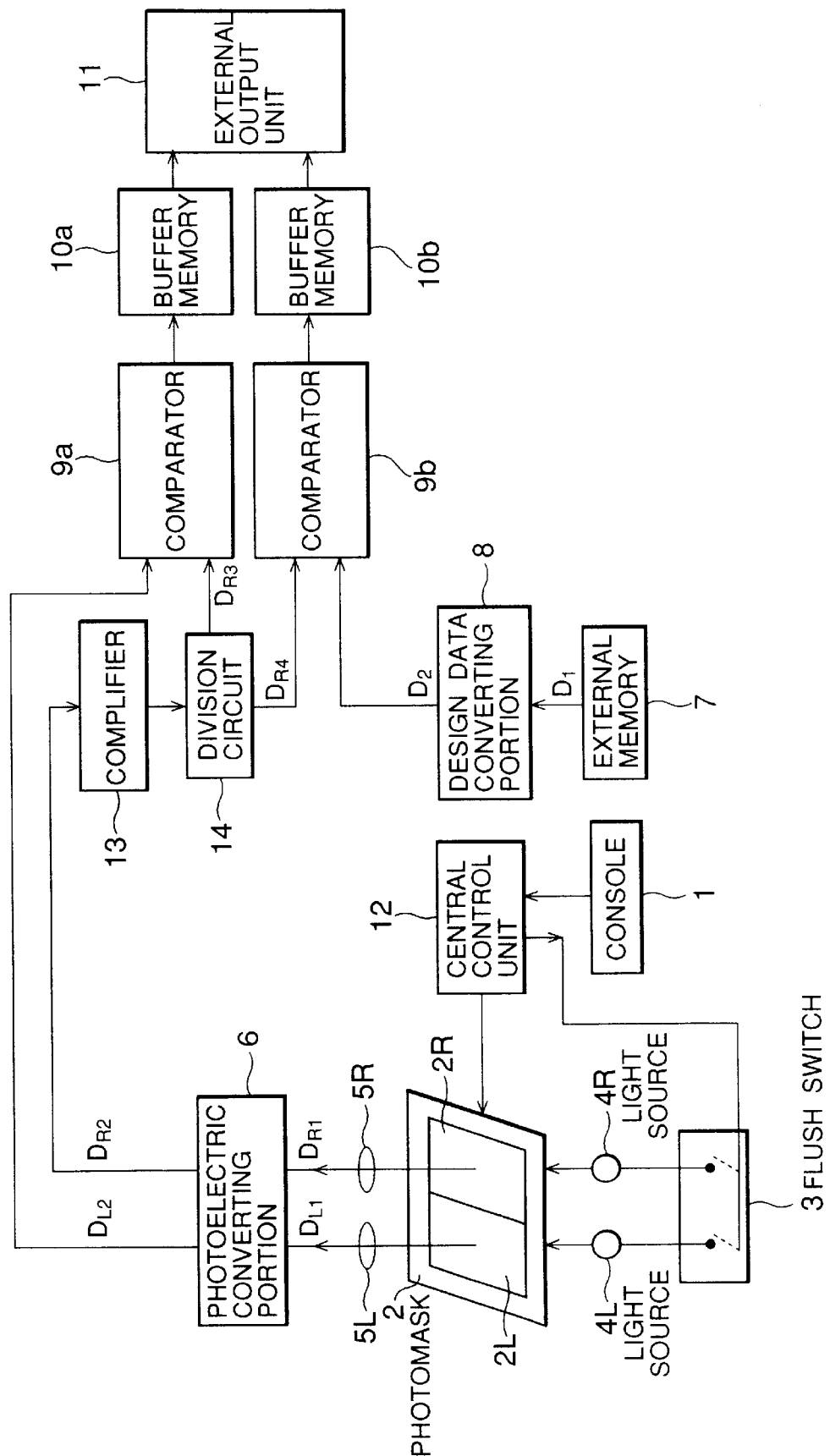
FIG. 2 is a structural view of an example of the prior art.

Referring now to FIG. 1, there is shown a photomask inspection apparatus according to an embodiment of the present invention, in which the same components as those in FIG. 2 are designated by the same reference characters to unit the further description thereof. In FIG. 1, this photomask inspection apparatus include a console 1 for inputting pattern information of a photomask 2, right and left two optical sources 4L and 4R connected to a flush switch 3 and for scanning right and left identical unit patterns 2L and 2R on the photomask 2, right and left two lenses 5L and 5R for focusing beams of light having passed through the right and left unit patterns 2L and 2R, a photoelectric converting portion 6 for converting the focused scanning beams into electrical signals, a design data converting portion 8 for reading design data stored in an external memory 7 to convert the data into an electrical signal, a comparator 9a for comparing the electrical signals obtained from the right and left unit patterns, buffer memories 10a and 10b for temporarily storing information of the right and left unit patterns respectively when the comparator 9a detects a difference between the right and left unit patterns, a division circuit 14 for dividing the electrical signal from the design data converting portion 8 into two electrical signals, comparators 9b and 9c for comparing the information of the right and left unit patterns stored in the buffer memories 10a and 10b with the electrical signals from the division circuit 14, a buffer memory 10c for temporarily storing defect information obtained from the comparators 9b and 9c, and an external output unit 11 for retrieving the defect information in the buffer memory 10c.

In operation, design data $D_1$ used for preparing the photomask 2 is inputted into the external memory 7, and the photomask 2 is attached to the apparatus. Next, pattern structure information is inputted from the console 1. This causes a central control unit 12 to operate so that the flush switch 3 turns on the light sources 4L and 4R.

The scanning beams from the light sources 4L and 4R pass through the right and left unit patterns 2L and 2R of the photomask 2 to be made optical signals $D_{L1}$ and $D_{R2}$, and further are focused by the right and left two lenses 5L and 5R onto a light receiving surface of the photoelectric converting portion 6 to be converted into comparison signals $D_{L2}$ and $D_{R2}$.

The comparator 9a compares the comparison signal $D_{L2}$ related to the unit pattern 2L of the photomask 2 with the comparison signal $D_{R2}$ related to the unit pattern 2R of the photomask 2. When the comparator has found the difference therebetween, the comparator inputs coordinate information d as defect information obtained by the pattern comparison method into the design data converting portion 8, and at the same time, the comparator inputs the comparison signals $D_{L2}$ and $D_{R2}$ as comparison signals $D_{L3}$ and $D_{R3}$ having differences into corresponding buffers memories 10a and 10b, respectively, so that the signals are temporarily stored therein.

On the other hand, the design data converting portion 8 generates an inspection signal $D_2$ for the periphery of the defect portion from the design data $D_1$ read from the external memory 7 on the basis of the coordinate information d inputted from the comparator 9a. The inspection signal $D_2$ is supplied to the division circuit 14, and is divided into two signals $D_3$ and $D_4$ by the division circuit 14.

The comparator 9b compares the comparison signal $D_{L4}$ read from the buffer memory 10a with the inspection signal $D_3$ taken from the division circuit 14. If the comparator finds a difference therebetween, defect information obtained by the database verifying inspection method is stored in the buffer memory 10c. Further, at the same time, the comparator 9c compares the comparison signal $D_{R4}$ read from the buffer memory 10b with the inspection signal $D_4$ taken from the division circuit 14. If the comparator finds a difference therebetween, defect information obtained by the database verifying inspection method is stored in the buffer memory 10c.

In this state, when an output instruction is inputted from the console 1, the defect information stored in the buffer memory 10c is outputted to the external output unit 11. As described above, in this embodiment, in the case where there is a difference between two adjoining unit patterns 2L and 2R (adjoining chips) formed on a photomask 2, the inspection signal $D_2$ of the periphery of the defect information portion is generated from the design data $D_1$ on the basis of the coordinate information d, and the inspection signal is compared with the two comparison signals related to the right and left unit patterns, so that it is possible to automatically determine which of the adjoining chips contains a defect.

Further, in this embodiment, the design data converting portion 8 is operated such that only in the case where there is a difference between the two comparison signals related to the right and left identical unit patterns 2L and 2R, the coordinate information d is generated and only the design data of the periphery of the defect information portion in the design data $D_1$ is converted to generate the inspection signal $D_2$. Thus, the apparatus of the present invention is able to shorten a data conversion time as compared with a conventional apparatus in which all the design data in the external memory 7 is converted, and the photomask inspection result can be quickly obtained.

As described above, according to the present invention, in the case where there is a difference between two adjoining identical unit patterns (adjoining chips) formed on a photomask, it is possible to automatically determine which of the adjoining chips contains a defect, so that it is possible to determined which of the chips contains a defect even if it is such a defect as an error in size of a contact hole, whereby more accurate photomask inspection can be executed as compared with the prior art.

Further, according to the present invention, in the case where there is a difference between the adjoining chips, only design data of the periphery of the coordinate information in all the design data is converted into an inspection signal, so that the data conversion time can be shortened as compared with the conventional apparatus in which all the design data in the external memory is converted, and the photomask inspection result can be quickly obtained.

It is apparent that the present invention is not limited to the above embodiment but may be changed and modified without departing from the scope and spirit of the invention.

What is claimed is:

1. A photomask inspection apparatus comprising:

a measuring system converting respective beams of light having separately scanned two adjoining identical unit patterns formed on a photomask into a first electrical signal and a second electrical signal, comparing the first and second electrical signals with each other to find whether or not the adjoining identical unit patterns are in conformity with each other, and when a nonconformity is found, outputting coordinate information of the nonconformity;

first and second memory circuits storing the first and second electrical signals, respectively, when the nonconformity is found by said measuring system;

a third memory circuit storing design data of a pattern formed on the photomask;

a design data converting portion selecting from the design data stored in the third memory circuit periphery data according to the nonconformity, and converting the periphery data to an inspection signal;

a first comparator comparing an output of the first memory circuit and the inspection signal; and a second comparator comparing an output of the second memory circuit and the inspection signal;

thereby judging which of the two adjoining identical unit patterns contain a defect.

2. The photomask inspection apparatus as claimed in claim 1, wherein the design data converting portion selects the periphery data from the design data stored in the third memory circuit according to the coordinate information of the nonconformity.

3. The photomask inspection apparatus as claimed in claim 1, wherein the measuring system comprises a third comparator comparing the first and second electrical signals with each other and outputting the coordinate information of the nonconformity to the design data converting portion.

4. A photomask inspection apparatus comprising:

a measuring system converting respective beam of light having separately scanned two adjoining identical unit patterns formed on a photomask into a first electrical signal and a second electrical signal, comparing the first and second electrical signals with each other to find whether or not the adjoining identical unit patterns are in conformity with each other, and when a nonconformity is found, outputting coordinate information of the nonconformity;

a design data converting portion inputting design data of the photomask, selecting from the inputted design data periphery data according to the nonconformity, and converting the periphery data to an inspection signal;

a first comparator comparing the first electrical signal and the inspection signal at the time the nonconformity found by the measuring system;

a second comparator comparing the second electrical signal at the time of the nonconformity found by the measuring system and the inspection signal;

thereby judging which of the two adjoining identical unit patterns contains a defect.

5. The photomask inspection apparatus as claimed in claim 4, wherein the design data converting portion selects the periphery data from the inputted data according to the coordinate information of the nonconformity.

6. The photomask inspection apparatus as claimed in claim 4, wherein the measuring system comprises a third comparator comparing the first and second electrical signals with each other and outputting the coordinate information of the nonconformity to the design data converting portion.

* * * * *